United States Patent [19]
Cundari et al.

[11] Patent Number: 5,916,180
[45] Date of Patent: Jun. 29, 1999

[54] CALIBRATING PRESSURE SENSORS

[75] Inventors: Michael A. Cundari, Hingham; Brian D. Noble, Weymouth; Troy W. Roberts, Pepperell; David R. Widder, Newton; Timothy Last, Lowell, all of Mass.

[73] Assignee: UroMed Corporation, Needham, Mass.

[21] Appl. No.: 08/943,344

[22] Filed: Oct. 3, 1997

[51] Int. Cl.⁶ .................................................. A61B 5/103
[52] U.S. Cl. ................................................ 600/587; 73/101
[58] Field of Search ................................. 600/988, 561, 600/587, 595; 73/1.01, 1.02, 1.03

[56] References Cited

U.S. PATENT DOCUMENTS

| | | | |
|---|---|---|---|
| Re. 30,446 | 12/1980 | Meyers et al. | 128/736 |
| Re. 32,000 | 10/1985 | Sagi | 128/736 |
| 3,154,789 | 11/1964 | Lewis, Jr. | 2/104 |
| 3,308,476 | 3/1967 | Kleesattel . | |
| 3,323,352 | 6/1967 | Branson . | |
| 3,744,490 | 7/1973 | Fernandez | 128/2.05 |
| 3,847,139 | 11/1974 | Flam | 128/2 H |
| 3,854,471 | 12/1974 | Wild | 128/2 V |
| 3,880,145 | 4/1975 | Blick | 128/2.05 |
| 3,970,862 | 7/1976 | Edelman et al. | 307/88 ET |
| 3,972,227 | 8/1976 | Tomilov | 73/67.7 |
| 3,996,922 | 12/1976 | Basham | 128/2 R |
| 4,001,951 | 1/1977 | Fasse | 35/17 |
| 4,023,562 | 5/1977 | Hynecek et al. | 128/2.05 E |
| 4,025,165 | 5/1977 | Sollish et al. | 350/161 S |
| 4,132,224 | 1/1979 | Randolph | 128/2 S |
| 4,134,218 | 1/1979 | Adams et al. | 35/17 |
| 4,135,497 | 1/1979 | Meyers et al. | 128/2 H |

(List continued on next page.)

FOREIGN PATENT DOCUMENTS

| | | |
|---|---|---|
| PCT/US96/17173 | 10/1996 | European Pat. Off. . |
| 2 086 575 | 5/1982 | United Kingdom . |

OTHER PUBLICATIONS

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast–Transfer Efficiency in Elastography: an Analytic Study", 1996, Ultrasound in Med. & Biol., vol. 22, No. 4, pp. 463–470.

(List continued on next page.)

*Primary Examiner*—Cary O'Connor
*Assistant Examiner*—Pamela L. Wingood
*Attorney, Agent, or Firm*—Fish & Richardson P.C.

[57] ABSTRACT

Methods and devices are described for calibrating the pressure sensors of a tissue examination device to enable the sensors to produce signals that accurately indicate whether an underlying tissue structure is present in tissue being examined. In general, the calibration is performed using a substance configured to apply a selected amount of pressure to the sensors when engaged in a selected way by the tissue examination device. The sensors are calibrated based on levels of the signals produced in response to the selected amount of pressure imposed by the substance. The tissue examination device may be pressed against the substance, or the substance may be pressed against the sensors. Preferably, the substance applies the selected amount of pressure substantially uniformly to the sensors. A wide variety of substances can be used, such as a foam pad, a rubber pad, a gel, a fluid-containing balloon, and pressurized air. The calibration methods and devices are simple to perform—and in fact are preferably performed during device power up so as to be transparent to the user—while accurately compensating for variations in the signals produced by the sensors as a group, as well as for individual (i.e., sensor to sensor) variations.

73 Claims, 8 Drawing Sheets

U.S. PATENT DOCUMENTS

| | | | |
|---|---|---|---|
| 4,144,877 | 3/1979 | Frei et al. | 128/2 S |
| 4,159,640 | 7/1979 | Leveque et al. | 73/81 |
| 4,190,058 | 2/1980 | Sagi | 128/736 |
| 4,212,306 | 7/1980 | Mahmud | 128/665 |
| 4,219,708 | 8/1980 | Rubey | 200/61.47 |
| 4,250,894 | 2/1981 | Frei et al. | 128/774 |
| 4,286,602 | 9/1981 | Guy | 128/665 |
| 4,291,708 | 9/1981 | Frei et al. | 128/734 |
| 4,458,694 | 7/1984 | Sollish et al. | 128/734 |
| 4,503,865 | 3/1985 | Shishido | 128/774 |
| 4,524,778 | 6/1985 | Brown, Jr. et al. | 128/736 |
| 4,555,953 | 12/1985 | Dario et al. | 73/862.04 |
| 4,570,638 | 2/1986 | Stoddart et al. | 128/665 |
| 4,600,011 | 7/1986 | Watmough | 128/664 |
| 4,641,659 | 2/1987 | Sepponen | 128/653 |
| 4,641,661 | 2/1987 | Kalarickal | 128/744 |
| 4,651,749 | 3/1987 | Sagi | 128/736 |
| 4,657,021 | 4/1987 | Perry et al. | 128/630 |
| 4,729,378 | 3/1988 | Trittenbass | 128/645 |
| 4,737,109 | 4/1988 | Abramson | 434/267 |
| 4,768,516 | 9/1988 | Stoddart et al. | 128/665 |
| 4,774,961 | 10/1988 | Carr | 128/736 |
| 4,790,329 | 12/1988 | Simon | 128/749 |
| 4,793,354 | 12/1988 | Wright et al. | 128/630 |
| 4,807,637 | 2/1989 | Bjorkhom | 128/664 |
| 4,810,875 | 3/1989 | Wyatt | 250/227 |
| 4,817,623 | 4/1989 | Stoddart et al. | 128/665 |
| 4,873,982 | 10/1989 | Morrison | 128/630 |
| 4,886,070 | 12/1989 | Demarest | 600/488 |
| 5,010,772 | 4/1991 | Bourland et al. | 73/862.04 |
| 5,012,817 | 5/1991 | Zeilinski et al. | 128/744 |
| 5,031,634 | 7/1991 | Simon | 128/754 |
| 5,079,698 | 1/1992 | Grenier et al. | 364/413.13 |
| 5,099,848 | 3/1992 | Parker et al. | 128/661.07 |
| 5,140,989 | 8/1992 | Lewis et al. | 128/665 |
| 5,143,079 | 9/1992 | Frei et al. | 128/734 |
| 5,212,637 | 5/1993 | Saxena | 364/413.26 |
| 5,221,269 | 6/1993 | Miller et al. | 604/281 |
| 5,265,612 | 11/1993 | Sarvazyan et al. | 128/660.01 |
| 5,301,681 | 4/1994 | DeBan et al. | 128/736 |
| 5,301,682 | 4/1994 | Debbas | 128/737 |
| 5,333,612 | 8/1994 | Wild | 128/660.9 |
| 5,524,636 | 6/1996 | Sarvazyan et al. | 128/660.9 |
| 5,678,565 | 10/1997 | Sarvazyan | 128/774 |
| 5,785,663 | 7/1998 | Sarvazyan | 600/587 |
| 5,795,308 | 8/1998 | Russin | 600/567 |
| 5,807,276 | 9/1998 | Russin | 600/567 |
| 5,833,634 | 11/1998 | Laird et al. | 600/587 |

OTHER PUBLICATIONS

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp. 111–117.

G.I. Pressman et al., "A Transducer for the Continuous External Measurement of Arterial Blood Pressure", 1960s, IEEE Transactions on Bio–Medical Electronics.

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel J. Med. Sci., pp. 859–864, Israel.

R.G. Stevens et al.,"The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

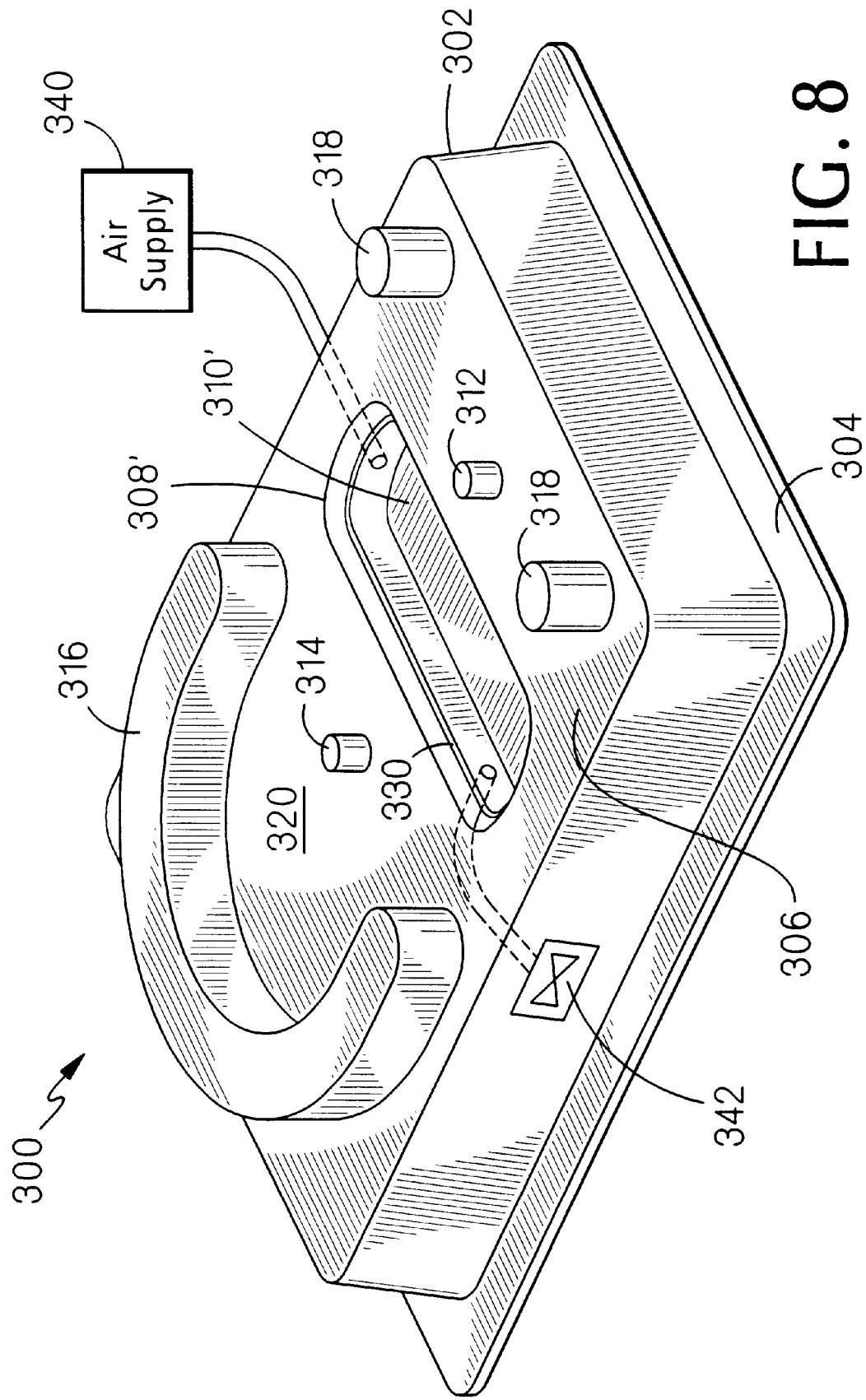

CALIBRATING PRESSURE SENSORS

BACKGROUND

This invention relates to calibrating pressure sensors on a tissue examination device.

All women are at risk for breast cancer. This risk increases as a woman ages. Women are generally considered to be at increased risk for developing breast cancer if they have one or more of the following risk factors: a family history of breast cancer, a previous diagnosis of a malignant breast tumor or other gynecological cancers, hormonal factors, or not having had any children or having a first child later in their child bearing years. Even so, the majority of all breast cancers occur in women who apparently do not have identifiable risk factors.

Although breast cancer currently cannot be prevented, it can be detected at an early, treatable stage when the tumor is small and has not spread beyond the breast. Women who are treated at this early stage have a much higher survival rate than women who are treated at more advanced stages of the disease. However, not all breast cancers are currently detected at this early stage. Therefore, the importance of screening for breast cancer has become a critical aspect in the overall management of this disease.

The methods currently used in the United States to screen for breast cancer and other breast conditions include monthly Breast self examination (BSE), mammography, and clinical breast examination.

Breast self examination is manual examination of a woman's breast tissue by the woman herself. During such examinations, a woman should examine her breasts at the same time each month, 7–10 days after the first day of her last menstrual cycle. She should report to her physician anything she feels that is new or that has changed since her prior exam.

Breast self examinations are important for the early detection of breast cancer. However, many women do not perform these examinations. When questioned about this, most women explain that they are not comfortable with their level of skill in doing such examinations. Products which help to remove the obstacles that prevent women from examining their breasts regularly would clearly be beneficial. Ideally, these products would increase the quality of such examinations without requiring extensive technical skill from their users.

Several devices designed to assist the user and clinicians in performing breast self examination are described in commonly-owned U.S. patent application Ser. No. 08/757, 466, entitled "Tissue Examination" (hereinafter, the '466 application), incorporated herein by reference. These devices include an array of sensors each of which produces a signal in response to the pressure imposed thereon as the sensor is pressed against tissue. The pressure varies in accordance with properties of different types of underlying tissue structures. Processing tests are performed on the signals to discern the characteristics of underlying tissue structures and thus discriminate between different types of underlying tissue (e.g., potentially foreign structures such as cysts or solid masses, and normal structures such as a nipple, a rib, or a ligament). Accordingly, the devices can alert the user to the presence of suspicious or indeterminate discrete and dominate structures in breast tissue.

Many of the processing tests performed by the devices described in the '466 application search for small differentials in the outputs of the pressure sensors. Random or patterned faults, due e.g. to the sensor state and not the underlying tissue, may produce erroneous test results, thereby potentially leading to "false positive" indications of potentially foreign tissue structures. Moreover, if some of the sensors respond unduly weakly to imposed pressure, the device may fail to detect an underlying structure (particularly if the weakened sensors are concentrated together in the array).

SUMMARY

This invention features methods and devices for calibrating the pressure sensors of a tissue examination device to enable the sensors to produce signals that accurately indicate whether an underlying tissue structure is present in tissue being examined. The calibration methods and devices are simple to perform—and in fact are preferably performed during device power up so as to be transparent to the user—while accurately compensating for variations in the signals produced by the sensors as a group, as well as for individual (i.e., sensor to sensor) variations.

In one general aspect of the invention, calibration is performed using a substance that is configured to apply a selected amount of pressure to the sensors when engaged in a selected way by the tissue examination device. Applying a selected, known amount of pressure to the sensors allows the responses of the sensors to be measured and adjusted as necessary to compensate for group-wide and individual variations.

Preferred embodiments may include one or more of the following features.

In some embodiments, the tissue examination device pressed against the substance; in other embodiments, the substance is pressed against the sensors. Preferably, the substance applies the selected amount of pressure substantially uniformly to the sensors. A wide variety of substance can be used. Examples include a foam pad, a rubber pad, a gel, a fluid-containing balloon, and pressurized air.

Preferably, the calibration device includes a fixture that supports the substance, for example, within a recess that receives a head of the tissue examination device on which the sensors are mounted. The fixture allows the head of the tissue examination device to be advanced by a selected distance into the recess. In some embodiments, the substance is deflected by the head of the tissue examination device when it is advanced by the selected distance, thereby applying the selected amount of pressure to the sensors. In embodiments in which the substance includes air, the recess may be sealed and the air in the recess pressurized to apply the selected amount of pressure to the sensors.

The fixture may include a portion (e.g., a projection on a surface of the fixture in which the recess is formed) which engages, e.g., a handle on the tissue examination device when the head of the tissue examination device has been advanced by the selected distance to limit further advancement of the head. In addition, the fixture surface may be configured to receive a portion of the handle when the head is received in the recess. These features both assure that the proper amount of pressure will be applied to the sensors, and give the user feedback that she has properly engaged the sensor head with the calibration device. Moreover, a portion of the fixture may also actuate a power switch on the tissue examination device when the head is received in the recess. As a result, the user both powers up the tissue examination device and starts the calibration procedure when she inserts the device in the fixture.

The sensors of the tissue examination device produce signals in response to pressure imposed thereon as the sensors are pressed against tissue, and are calibrated based on levels of the signals produced in response to the selected amount of pressure imposed by the substance. Preferably, the calibration is performed in two stages. In the first stage, the calibration is performed for the plurality of sensors as a whole, while in the second stage the calibration is performed for the sensors individually.

The first calibration stage is performed to cause calibrated signals to be generated based on the signals produced by the sensors, the calibrated signals having levels that change by a selected average amount in response to a selected amount of change in the pressure imposed on the sensors. The second stage of calibration is performed so that the signal from each sensor has a selected range of levels that corresponds to a selected range of applied pressures. The selected range of levels is, for example, between a zero level that corresponds to the applied pressure when the sensor is not pressed against tissue, and a maximum level that corresponds to a maximum expected applied pressure when the sensor is pressed against tissue that contains an underlying tissue structure to be detected by the tissue examination device.

In another aspect of the invention, the calibration device causes operating power to be applied to the processor only when it is engaged in the selected way with the tissue examination device. This feature prevents the tissue examination device from being used to examine tissue unless it has been calibrated. Accordingly, the risk of inaccurate results caused by sensors that are out of calibration is minimized. Moreover, this feature ensures that calibration is performed every time that the tissue examination device is used, thereby allowing the calibration procedure to compensate for slowly changing sensor variations that are caused, e.g., by wear.

In a preferred embodiment, the tissue examination device includes a power switch for its processor, and a portion of the calibration device actuates the power switch when the tissue examination device is engaged with the calibration device in the selected way (e.g, inserted in the recess and engaged with the pressure applying substance, as discussed above).

Another aspect of the invention features a tissue examination device that includes a plurality of pressure sensors mounted on a sensor head, each of the sensors producing signals in response to pressure imposed thereon as the sensor is pressed against tissue, and a processor for processing the signals to detect whether an underlying tissue structure is present in the tissue being examined. A calibration device for the tissue examination device includes a substance adapted to be engaged in a selected way by the sensor head and configured to apply a selected amount of pressure to the sensors when so engaged, and circuitry for calibrating the sensors based on the levels of the signals that are produced by the sensors in response to the selected amount of pressure imposed by the substance.

Preferred embodiments may include one or more of the following features.

The calibration circuitry performs the calibration in the two stages discussed above (i.e., for the sensors as a whole and for the sensors individually). Calibration is performed based on a first set of signals acquired from the sensors when the head is engaged with the substance and the selected amount of pressure has been imposed on the sensors thereby, and a second set of signals acquired from the sensors when the head is not engaged with the substance. The first and second sets of signals are stored in a memory.

A gain is applied to the signal acquired by each one of the sensors. During the first calibration stage, a calibrated gain is determined based on the first and second sets of signals, and the applied gain is changed to the calibrated gain thereby to calibrate the plurality of sensors as a whole. Preferably, an average level of the first set of signals and an average level of the second set of signals is determined, and the calibrated gain is determined based on these average levels.

In the second calibration stage, individual correction factors are determined for individual sensors based on the first and second sets of signals, and the correction factors are stored in the memory. The correction factors are applied to the signals generated by the sensors when the tissue examination device is pressed against tissue to generate corrected signals, and the corrected signals are processed to detect whether an underlying tissue structure is present in the tissue being examined. During examination, the user is notified if an underlying tissue structure has been detected.

A determination is made, e.g., at the end of the calibration procedure, as to whether the calibration was successful. If the calibration was successful, the user is notified that examination of tissue with the tissue examination device may proceed. The processor is disabled from further operation if the calibration is determined to have been unsuccessful.

The invention allows tissue examination devices to include relatively inexpensive, readily available pressure sensors, while also providing an easy to use, yet accurate, way of calibrating the sensors to compensate for variations caused by a host of different factors (e.g., manufacturing variations, stresses imposed on the sensors by the construction of the tissue examination device, environmental changes, and wear). Indeed, the calibration procedure is transparent to the user beyond the step of powering up the device. Performing calibration as part of the power up procedure ensures that the device is properly calibrated before each use, thereby minimizing the risk of inaccurate detection (e.g., false positive readings) without requiring the user to follow a series of complex calibration steps.

Other features and advantages of the invention will become apparent from the following detailed description, and from the claims.

DRAWINGS

FIG. 8 shows an alternative calibration fixture.

DETAILED DESCRIPTION

Figure 1:
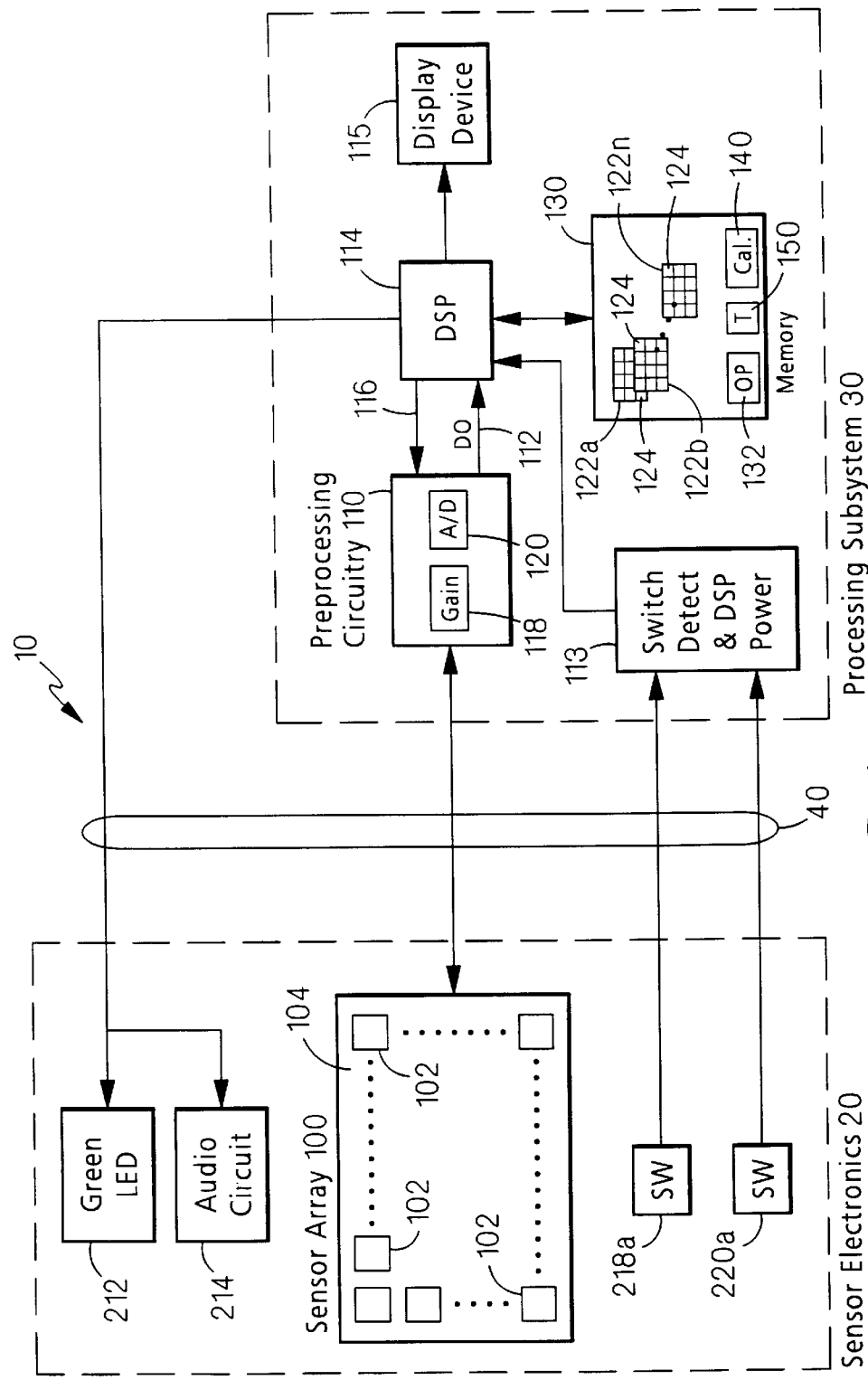
FIG. 1 is a block diagram of a tissue examination device having an array of pressure sensors.
Figure 2:
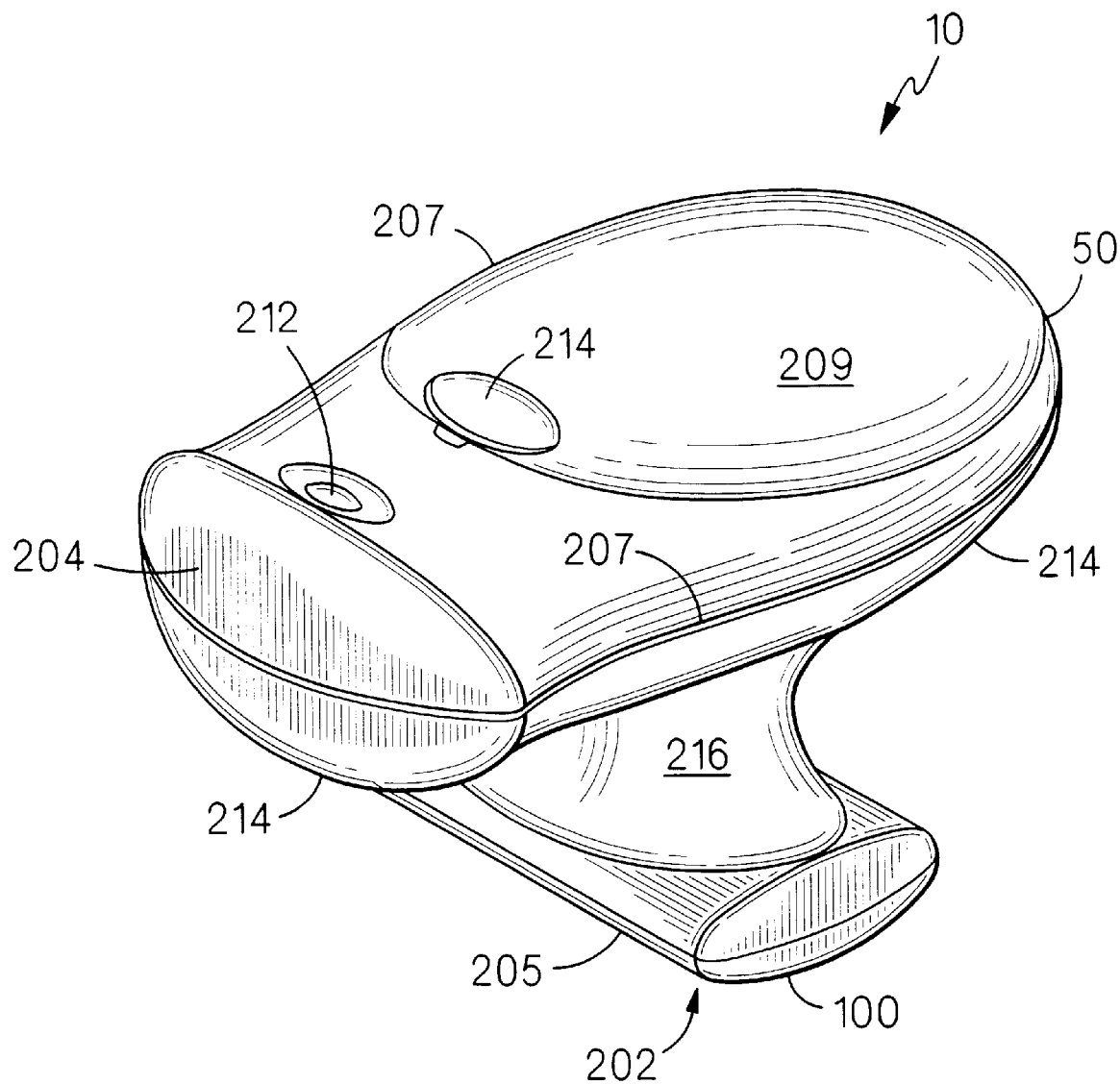
FIG. 2 is a perspective view of the tissue examination device.

Referring to FIGS. 1 and 2, tissue examination device 10 includes sensor electronics 20 connected to a processing subsystem 30 via a cable 40, all of which are mounted in a housing 50. As described in the '466 application, sensor electronics 20 include an array 100 of pressure sensors 102 carried on a thin, flexible membrane 104. Array 100 is, for example, a contact sensor such as that described in U.S. Pat. No. 4,856,993, entitled "Pressure and Contact Sensor System for Measuring Dental Occlusion" (the '993 patent), incorporated herein by reference, the individual pressure sensors 102 of which are resistive elements. Pressure sensors 103 are arranged in an orthogonal grid of rows and columns in array 100. Pressure sensors 102 are relatively small and are closely spaced to provide high resolution capable of distinguishing between areas of underlying tissue separated by 1 mm or less. Array 100 is commercially available from Tekscan, Inc. (the assignee of the '993 patent).

Housing 50 comprises an integral sensor head 202 and handle 204 made from a rigid polymer such as polycarbonate. Sensor array 100 is mounted on a lower surface 205 of head 202, with sensors 102 being exposed beneath head 202 for contacting the tissue. Lower surface 205 is convex, with a radius of curvature of approximately 1.5 inches to enhance the mechanical coupling between sensors 102 and the underlying tissue. The mechanical coupling can also be improved by lubricating the tissue to be examined (e.g., the breast) with a suitable lubricating agent, such as a gel. In use, the user grasps handle 204 and presses sensor head 202 against the breast and manually moves head 202 across the lubricated skin to translate sensor array 100 over the tissue. The translation technique is essentially a series of stationary palpations which allow the user to increase breast area coverage with less exam time.

Handle 204 is shaped to be conveniently grasped by a user to comfortably place array 100 against the breast, and the longitudinal axis of handle 204 is orthogonal to that of head 202. Specifically, the side surfaces 207 and upper surface 209 of handle 204 are curved as shown to allow handle 204 to be held in the palm of the hand with the longitudinal axis of head 202 arranged generally in the same direction as the user's forearm. This allows the user to maintain sensor head 202 (and hence sensor array 100) against the breast during the examination without bending or otherwise straining the wrist.

Figure 4A:
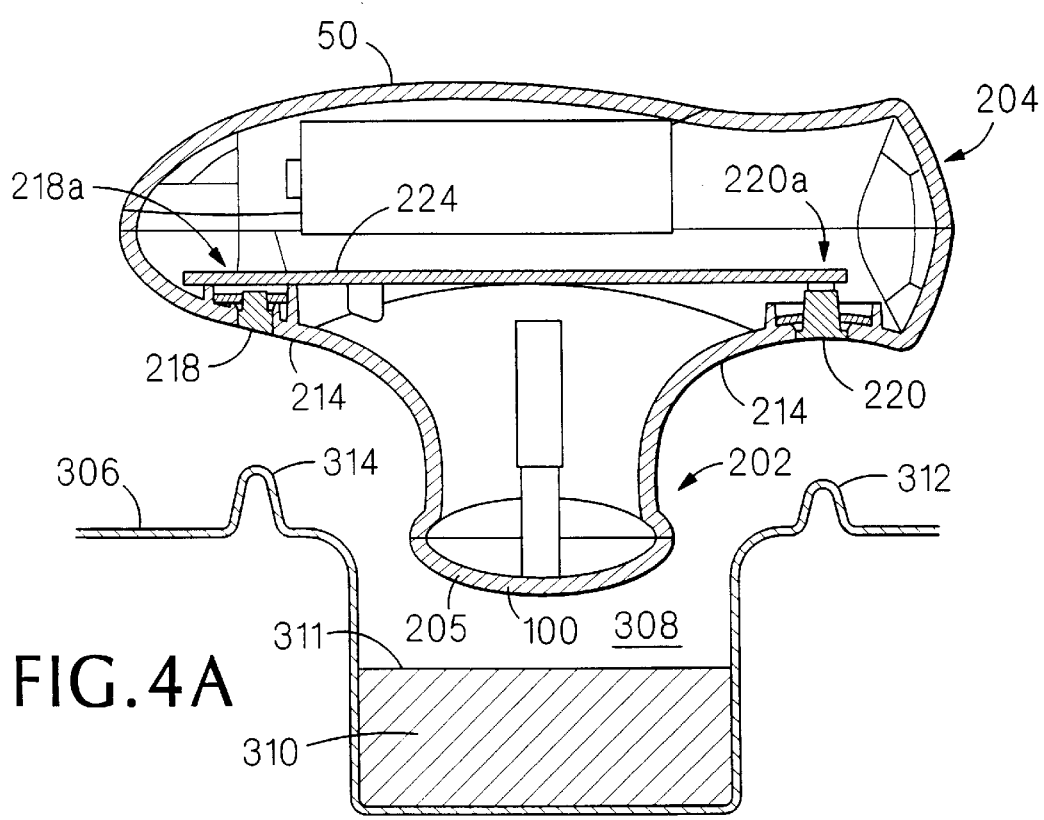
FIGS. 4A and 4B show the use of the tissue examination device with the calibration fixture during calibration.
Figure 4B:
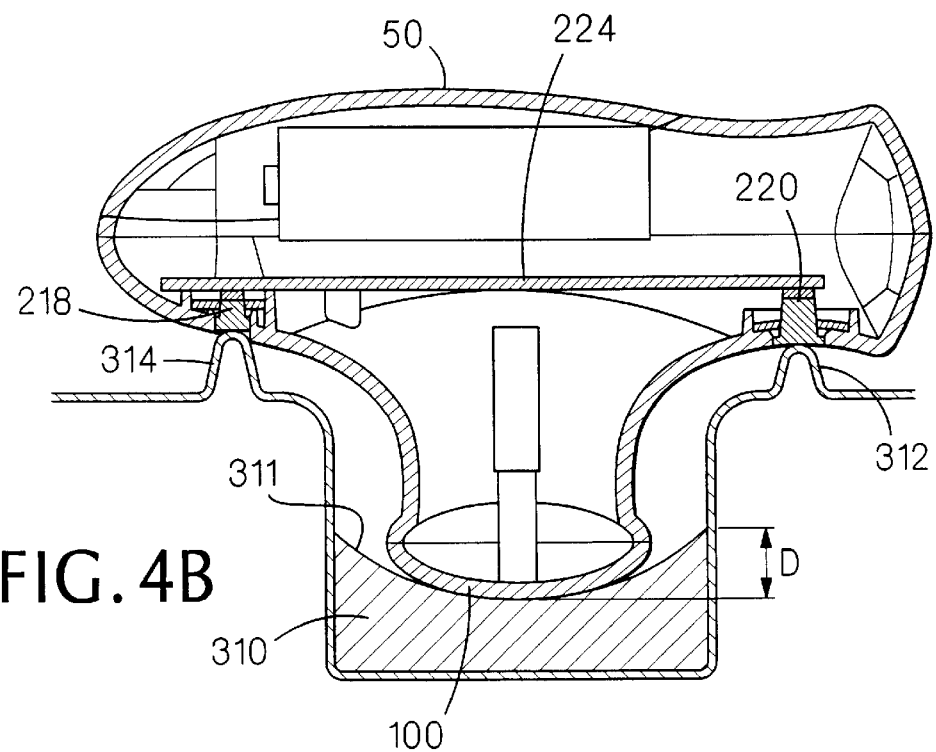

As also shown in FIGS. 4A and 4B, the underside 214 of handle 204 smoothly meets a tapered neck 216 which connects handle 204 to sensor head 202. The surfaces of neck are also curved to allow for easy manipulation by the user. A pair of switch contacts 218, 220 for corresponding device 10 power switches 218a, 220a are supported on underside 214 for purposes to be described. Suffice it here to say that switch contacts 218, 220 are normally in the "open" position and are actuated during calibration of sensor array 100 to close a pair of contacts of respective switches 218a, 220a (FIG. 1) mounted on a printed circuit board 224 within handle 204. The closure of both switches 218a, 220a is detected (via cable 40) by a circuit 113 in subsystem 30, which responds by applying operating power to DSP 114. Thus, device 10 cannot be calibrated or used to examine tissue without closing switch contacts 218, 220. Switch contacts 218, 220 are recessed within handle 204 to avoid accidental actuation.

The resistance of each pressure sensor 102 changes in accordance with the amount of pressure applied to sensor 102. The resistance change is inversely proportional to the pressure imposed on sensor 102. Thus, the resistance of each sensor 102 decreases as applied pressure increases. Generally, the pressure imposed on sensors 102 increases when sensors 102 are pressed against localized areas of stiffer tissue on, within, or below the softer breast tissue. Examples of such stiffer tissue include normal breast tissue structures—such as the nipple, the inframammary ligament, and underlying ribs—and foreign bodies such as cysts and solid masses (whether or not pathogenic). Consequently, as array 100 is pressed and moved against the breast, the pressure imposed on sensors 102 and, thus their resistance, varies in accordance with the properties of the underlying tissue structures.

The individual resistances of pressure sensors 102 are read by preprocessing circuitry 110 (FIG. 1), which produces corresponding digital output (DO) signals 112 that are applied to a digital signal processor (DSP) 114. Briefly, preprocessing circuitry 110 sequentially measures the resistance of pressure sensors 102 in response to row and column address signals 116 provided by DSP 114 to provide an indication of pressure applied to the location in array 100 that corresponds to that sensor 102. During each resistance measurement, preprocessing circuitry 110 applies a reference potential (not shown) to the addressed sensor 102 and measures the resulting voltage drop induced across that sensor 102. Preprocessing circuitry amplifies this voltage in gain stage 118 to scale the measured voltage drop to desired levels. (As discussed in detail below, one of the adjustments made during calibration is to the amplification (i.e., gain) applied by gain stage 118.)

The amplified voltage levels are then digitized by A/D converter 120 to produce the digital output (DO) signals 112 the values of which correspond to the resistance-induced voltage drops. (Alternatively, DSP 114 can perform the digitization.) In this way, each pressure sensor 102 produces a DO signal 112 having a digital value that represents the pressure applied to that sensor 102. The operation of preprocessing circuitry 110 is more fully described in the '993 patent.

The set of sequentially produced DO signals 112 for all pressure sensors 102 in array 100 is termed a "frame." DSP 114 addresses preprocessing circuitry 110 at a rate sufficient to read 8 frames or more of DO signals 112 per second. DSP 110 stores each frame of DO signals 112 in an area 122a–122n of memory 130. Each memory area 122a–122n contains storage locations 124 which respectively correspond to the locations of pressure sensors 102 in array 100. Thus, each memory area 122a–122n contains a "map" of the pressures detected by pressure sensors 102 in a frame. This map can be viewed as a "pressure signature" of the tissue structures beneath array 100. Accordingly, memory areas 122a–122n contain a time sequence of pressure signatures of the underlying tissue as array 100 is palpated across the breast.

Housing 50 may also include a communication port (not shown) for coupling the maps of the array of DO signals 112 to a display device 115, thereby allowing the user to observe the pressure signatures directly. DSP 114 may also display the pressure signatures as images on display device 115 in a variety of ways, as described in commonly owned patent application entitled "Clinical Tissue Examination," filed on Sep. 16, 1997 (hereinafter, "the CTE application"), which is incorporated herein by reference. DSP may also perform additional processing to enhance the displayed images and provide further discrimination, as described in the CTE application. In addition, tissue examination device 10 may include the features, and perform the processing, discussed in commonly owned patent application Ser. No. 08/782,442 entitled "Tissue Examination" (hereinafter, "the '442 application"), which is incorporated herein by reference.

As described in the '466 application, different types of tissue structures have different pressure signatures which can be used to differentiate the tissue structure types from each other. The pressure signatures result from the way in which the tissue structures respond to being stressed by the pressures exerted when the user moves array 102 over the breast. The stiffness (elasticity) of a given tissue structure, its composition (e.g., percentage of fat, presence of ducts, and fibrous tissue), its density, and the degree to which the tissue structure is held in place by surrounding tissue are all factors that contribute to the pressure signature of the tissue structure. Another factor which affects the resulting pressure signature is whether anatomical structures (e.g. ribs) lie beneath the tissue structure. These factors, in combination, are sufficiently different for various types of tissue structures (e.g., normal breast structures such as ribs, nipples, ligaments, etc., and foreign structures such as cysts, solid masses, and other lumps with respect to normal tissue stiffness) that the pressure signatures of these structures are distinguishable from each other.

DSP 114 performs various processing tests (described in detail in, e.g., the '466 application) defined by an operating program (OP) 132 stored in memory 130 on the pressure signatures stored in memory areas 122a–122n. The tests enable DSP 114 to discriminate normal underlying tissue structures from potentially foreign structures. If DSP 114 determines a potentially foreign tissue structure is present, DSP 114 notifies the user by sounding an alarm (e.g., a chirping sound) using an audio circuit 214 in handle 204 (FIGS. 1 and 2). A green LED 212 is illuminated when tissue examination device is powered on and calibrated, as described below.

As discussed above, the pressure signatures are a function of the amount of average pressure applied to sensors 102 when the user presses array 100 against the body. Thus, the pressure applied by the user should be within a selected range in order for the pressure signatures to accurately correspond to the various tissue structure types. The limits of the pressure range are a function of the maximum expected peak of a detected underlying tissue structure when the average pressure measured by sensors 102 is within the tone range described herein. For array 100 discussed above, the range of pressures to be measured by sensors 102 is 0 psi to 5 psi.

Because the proper amount of user-applied pressure is important, DSP 114 examines each frame to determine whether the average amount of pressure applied to all sensors 102 is within an acceptable range (e.g., 0.5 psi to 2.0 psi). DSP 114 also determines if a minimum number of sensors 102 are obtaining a reading across width of array 100 such that DSP 114 recognizes that entire array 100 is in contact with the skin. If the frame fails either of these inquiries (e.g., if the user is applying an incorrect amount of pressure to the tissue with device 20), the frame is considered invalid and is not examined further in the test procedure. Otherwise, DSP 114 triggers audio circuit 214 to produce a low pitched humming tone. DSP 114 maintains this tone throughout the tissue examination (as long as the user is applying pressure within the correct range) to give the user feedback that the applied pressure is correct.

The various processing tests and other procedures performed by DSP 114 on output signals 112 are described in the above-referenced applications and will not be repeated here. The accuracy of these tests and procedures—and thus the reliability of the feedback given (e.g., by audio circuit 214) to the user as to the presence or absence of a potentially foreign underlying structure in the tissue—is dependent on the accuracy of the signals produced by pressure sensors 102. We have identified several potential sources of errors in the signals produced by sensors 102, and have developed a calibration device and procedure for calibrating sensors 102 to minimize, and preferably eliminate, these errors.

Some of the errors are a result of the structure of sensors 102. As discussed above, array 100 is commercially available from Tekscan, Inc. (the assignee of the '993 patent). Sensors 102 are essentially force sensitive resistors (FSR's) whose resistance decreases with increasing load (pressure). Because of manufacturing variations in e.g., the material used for the FSRs and the way in which each FSR sensor is formed on membrane 104, different arrays 100 of sensors may respond differently (e.g., produce a larger or smaller average resistance change) to a given applied pressure. These manufacturing variations may also cause individual sensors 102 within an array 100 to respond differently to a known applied pressure, thereby causing array 100 to produce a nonuniform output (i.e., pressure map) in response to pressure applied uniformly to the array. Another cause of variation is sensor wear. For example, average sensor output may degrade by 50% or more with extended use.

In addition, the way in which sensor array 100 is mounted on sensor head 202 (FIG. 2), and the curved nature of lower surface 205, imposes stresses on some of the sensors 102 that affect the sensor outputs. Array membrane 104 is attached to head lower surface 205 with adhesive. Wrapping membrane 104 over a curved surface generates a higher tension in some portions of membrane 104, thereby imposing a pre-load on some sensors 102. The pre-load causes these sensors 102 to produce an output signal when no external load is applied (i.e., when the sensors are not pressed against a substance such as tissue). Typically, these preloaded sensors 102 are grouped together in array 100, and thus their preloaded output can resemble a lump-like cluster (or "hot spot") of pressures, which may incorrectly indicate the presence of an underlying tissue structure. The preloading can initially be quite high, and may decrease over time as membrane 104 and adhesive creep on sensor head 202. The pre-load is also variable from sensor-to-sensor due to local variations in adhesive thickness, FSR material, and tension.

These error sources can have a large impact on the accuracy of the tissue examination (e.g., by producing false positive readings) unless sensors 102 are calibrated to counteract these effects. For example, initial clinical testing using tissue examination device 10 without calibration as described herein found that 40% of detections of underlying tissue structures were attributable to sensor-to-sensor variations. Calibrating sensors 102 as described below eliminates not only variations among arrays 100 of different tissue examination devices 10, but also variations between the individual sensors 102 of a given array 100.

Figure 3:
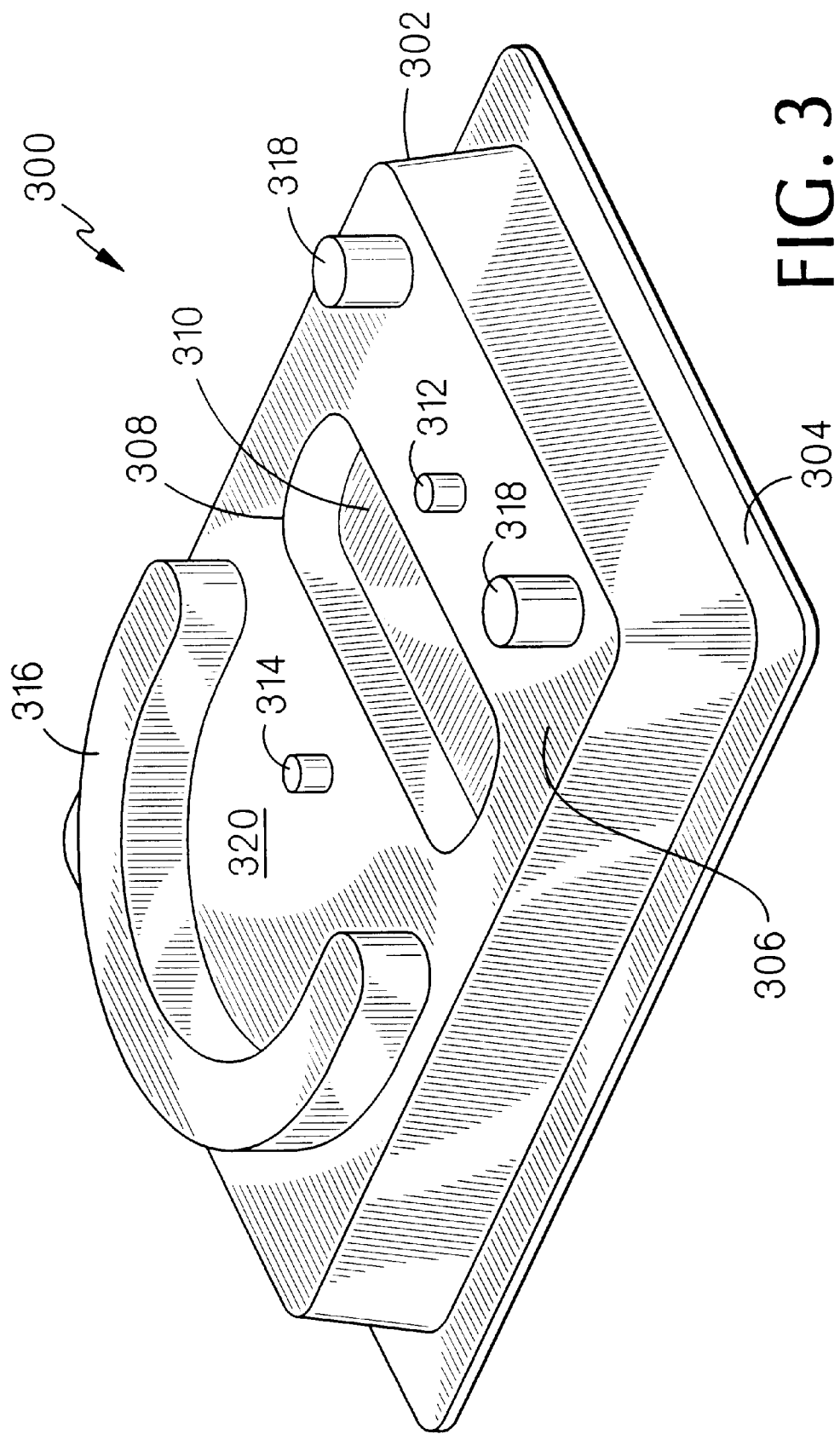
FIG. 3 is a perspective view of a calibration fixture used during calibration of the tissue examination device.

Referring to FIGS. 3, 4A, and 4B, sensors 102 are calibrated upon power-up of tissue examination device 10 prior to performing the tissue examination using fixture 300 that includes a fixture tray 302 supported by a thin, enlarged base 304. The upper surface 306 of tray 302 is provided with a recess 308 configured to receive sensor head 202 of tissue examination device housing 50 (FIG. 2). That is, recess 308 has length and width dimensions that correspond to those of sensor head 202. A compliant substance in the form of a pad 310 is disposed in recess 308 for engaging sensor head lower surface 205 and applying a selected amount of pressure to sensors 102 during the calibration procedure, as discussed below.

Pad 310 is made from a substance having a compliance that mimics that of the tissue being examined (in this example, breast tissue. As described below, fixture 300 is constructed to allow sensor head 202 to be advanced by a selected, limited distance against pad 310. Accordingly, pad 310 will be deflected by a known amount during calibration. The substance of pad 310 should exert a predetermined, selected amount of pressure (for example, 1 psi) against sensors 102 in response to this selected amount of deflection of pad 310. Further, the selected amount of pressure should be exerted uniformly over the area of pad upper surface 311 (FIGS. 4A, 4B) to exert the pressure evenly against all sensors 102 in array 100. We have found that foam has these characteristics and thus is a good choice for the substance of pad 310. Other substances may alternatively be used, as discussed below.

One factor that affects the amount and uniformity of the pressure exerted by the foam is the thickness of pad 310. The cell size (and thus the relative coarsity) of the foam also affects the uniformity of the pressure that the foam exerts against a deflecting object. A smaller cell size (and hence a more "fine" foam) can be expected to exert a more uniform pressure in response to deflection than a more coarse foam. We have found that a commercially available foam with the trade name "Nolatex" manufactured by Lendell, Inc. of St. Charles, Minn. to be a good choice for the material of pad 310.

Another factor that affects the uniformity of the pressure exerted by pad 310 against sensors 102 is the uniformity of the deflection force applied by sensor head 202 against pad 310. The deflection force will be most uniform if head 202 is inserted into recess 308 and pressed against pad 310 along a straight line that is perpendicular to fixture upper surface 306, rather than at an oblique angle to surface 306. Fixture 300 includes several features to help the user properly insert sensor head 202 perpendicularly into recess 308 and maintain this orientation while pressing sensors 102 against pad 310.

First, a pair of projections 312, 314 are mounted on upper fixture surface 306 on opposite sides of recess 308 for engaging and closing housing switch contacts 218, 220 when sensor head 202 is properly and fully inserted into recess 308 as described below, as can be seen by comparing FIGS. 4A and 4B. Circuitry 113 in subsystem 40 (FIG. 1) requires both switches 218a, 220a, to be closed by their respective contacts 218, 220 before applying power to DSP 114 and enabling signal processing to be performed. If head is not straightly inserted (i.e., perpendicularly) into recess 308, one switch contact 218, 220 might be engaged and closed by a projection 312, 314, but both contacts 218, 220 will not be so engaged. Accordingly, power will not be applied to DSP 114, the calibration procedure will not begin, and green LED 212 will not be illuminated to signal the user that the examination can proceed, unless the user properly inserts housing 50 into fixture 300. The recessed nature of contacts 218, 220 also avoids accidental, simultaneous actuation by anything other than projections 312, 314.

The engagement between projections 312, 314 and switch contacts 218, 220 also provides feedback to the user that sensor head 202 has been advanced by a selected distance against pad 310, and limits further advancement of head 202. Accordingly, projections 312, 314 help ensure that sensor head 202 is advanced by a distance D (FIG. 4B) (e.g., approximately 0.8 inches) selected to cause pad 310 to exert a known amount of pressure (e.g., 1 psi) against sensors 102. Of course, several factors contribute to allowing head 202 to be advanced by selected distance D, including the spacing between sensor head lower surface 205 and handle underside 214, the depth of recess 308, the thickness of pad 310, and the height of projections 312, 314.

A concave cradle 316 and a pair of posts 318 are also mounted on fixture surface 306. A cavity 320 defined by cradle 316 and the spacing between posts 318 are sized to approximately correspond to the width of sensor housing handle 204 (i.e., the dimension of handle 204 that extends in the same direction as the longitudinal axis of sensor head 202). Cradle 316 and posts 318 thus guide handle 204 as sensor head 202 is inserted into recess 308 to help ensure that switch contacts 218, 220 are engaged by projections 312, 314. Cradle 316 and posts 318 also allow the user to firmly seat housing 50 on fixture 300 during the calibration procedure to provide the user with positive assurance that sensor head 202 is properly engaged against pad 310.

Thus, in sum, the construction of fixture 300 and the configuration of tissue examination device housing 50 cooperate to allow sensor head 202 to be received within recess 308 and advanced by a selected distance D with respect to the fixture so that pad 310 applies a selected amount of pressure (e.g., 1 psi) uniformly to all sensors 102 during calibration. It is this exertion of a known amount of pressure against sensors 102 that allows the above-described sensor variations to be corrected (both for array 100 as a whole and from sensor to sensor within array 100), thereby increasing the accuracy with which tissue examination device 10 can detect underlying tissue structures.

The calibration procedure will now be described. Briefly, DSP 114 follows calibration instructions (Cal.) 140 stored in memory 130 (FIG. 1) to perform the calibration in two stages. In the first stage, a global calibration is performed to cause the DO signals 112 produced by all sensors 102 in array 100 to have an average sensitivity of 50 DO/psi. (That is, on average, the DO signals 112 from sensors 102 will have values of 50 in response to an applied pressure of 1 psi, values of 100 in response to 2 psi of applied pressure, and so on.) This is done by adjusting the overall gain provided by preprocessor gain stage 118. In the second stage (also called "equilibration"), each sensor 102 is calibrated individually to: (1) remove the effects of any preloading (i.e., to cause each sensor's DO signal value to be zero when sensor head 202 is not pressed against an object, such as the breast), and (2) cause the sensor to have an actual sensitivity of 50 DO/psi, thereby correcting the above-discussed sensor to sensor variations.

The calibration mathematics require that two pressure readings be taken from sensors 102 to fit a desired linear curve in adjusting the overall gain provided by preprocessor gain stage 118 during the first calibration stage. In addition, two full frames of output signals 122 from sensors 102 are required to generate the matrices used during the equilibration portion of the calibration procedure to adjust each individual sensor 102 of array 100 and create an uniform sensor image in response to a uniformly-exerted pressure.

Preliminarily, the calibration procedure is performed at 1 psi because this pressure approximates the nominal load on sensors 102 during normal tissue examination, thereby minimizing the impact of any errors or non-linearity. Moreover, the calibrated sensitivity of 50 DO/psi was chosen based on initial clinical tests of tissue examination device 10 using the Tekscan array 100 discussed above. These tests indicated that the peak signal generated by a suspicious or indeterminate discrete and dominate structure in breast tissue is approximately 5 psi. Thus, during calibration A/D converter 120 (which is an 8 bit device and thus has a maximum output of 255) is tuned to saturate at just over 5 psi, thereby providing maximal data resolution without saturation (i.e., 5 psi * 50 DO=250 DO) for this application.

Figure 5:
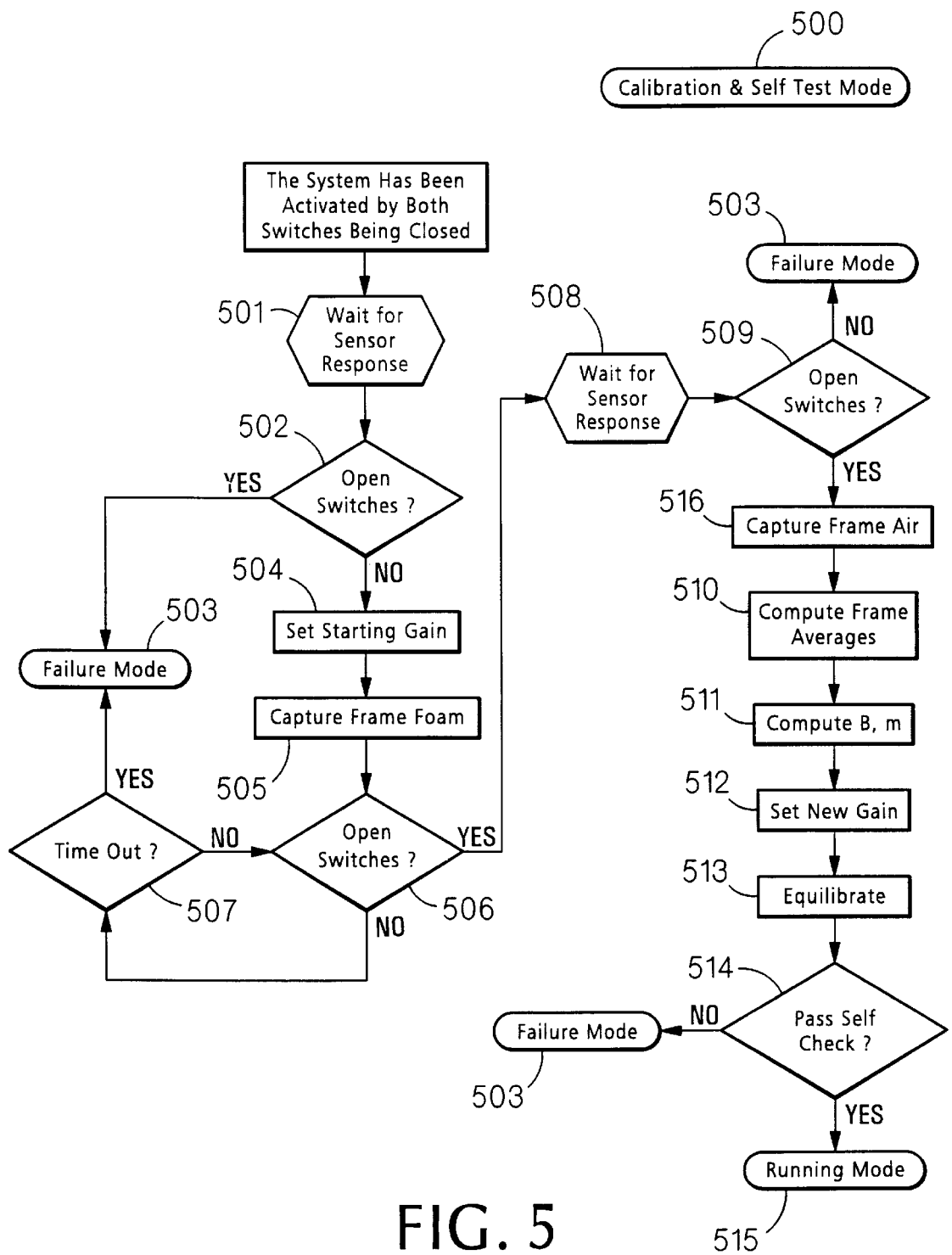
FIG. 5 is a flow chart of the calibration procedure.

Referring to FIG. 5, DSP 114 acquires two frames of signals from sensors 102 to obtain the necessary pressure readings. One frame is acquired when sensor head 202 has been pressed into fixture pad 310 by the selected distance, and a second frame is acquired in the ambient condition after tissue examination device housing 50 has been removed from fixture 300. FIG. 5 also illustrates some error traps to determine if the user has performed the calibration incorrectly.

The user powers-up device 10 and begins the calibration and self-test procedure 500 by properly inserting housing 50 into fixture 300. Only then will both switch contacts 218, 220 on device handle 204 be depressed by projections 312, 314 (FIG. 4) to close switches 218a, 220a (FIG. 1). As discussed above, both switches must be closed in order for circuitry 113 to apply operating power to DSP 114 and enable the calibration procedure to be performed. Whenever both switches 218a, 220a are closed, sensor head 202 has been advanced by the selected distance D to cause pad 310 to apply the selected amount of force (e.g., 1 psi) to sensors 102.

Upon power-up, DSP 114 waits momentarily to ensure that all dynamic mechanical and electrical transients in sensor array 100 have occurred (step 501) and then rechecks the switch contacts (step 502). If either switch 218a, 220a has opened, device 10 is no longer properly seated in fixture 300, and DSP 114 responds by entering a failure mode (step 503). Whenever DSP enters the failure mode, it activates audio circuit 214 on tissue examination device 20 to produce a "chirping" sound to signal the user that she has improperly seated device 20 in fixture 200 and waits a selected amount of time for the user to take corrective action (for example, by adjusting the position of housing 50 in fixture 300). If the user takes the action in a timely manner, the calibration procedure is restarted. Otherwise, circuitry 113 powers down DSP 114.

If the switches remain closed, DSP 114 resets a starting gain value (e.g., 0.55) in pre-processing circuitry gain stage 118 (step 504). This step is performed because calibration procedure 500 is followed—and the gain of gain stage 118 may be adjusted—every time the user operates device 10. Resetting the starting gain value ensures that preprocessing circuitry 110 has a known gain level at the start of each calibration. Because of the way in which preprocessing circuitry 110 acquires the signals from the sensor array (as described in the '993 patent), the gain is applied by gain stage 118 to the signals before they are multiplexed, digitized, and sent to DSP 114. Therefore, the gain affects the DO signals 112 of all sensors 102 uniformly.

DSP 114 then captures a frame of the amplified and digitized output (DO) signals 112 from sensors 102 (step 505)—i.e., a frame of signals generated by sensors 102 in response to the 1 psi pressure uniformly applied to array 100 by foam pad 310. The initial gain is applied to these signals by gain stage 118, and the frame (which we will call the "first frame") is digitized and stored by DSP 114 in memory 130. DSP 114 signals audio circuit to emit a single, brief chirp when the first frame is captured to notify the user that device 10 can be removed from the fixture.

The user then removes tissue examination device 10 from fixture 300 to allow an ambient (i.e., no pressure) frame to be acquired and stored. DSP 114 determines whether device 10 has been removed by entering a loop in which DSP 114 checks whether switches 218a, 220a have been opened (step 506). If either switch remains closed (e.g., if the user maintains device 10 within the fixture), DSP 114 enters a timeout check routine (step 507) to determine if it has been checking for an open switch condition for more than one minute. If the routine times out, DSP 114 determines that device 10 is being calibrated improperly, enters the failure mode discussed above (step 503), and notifies the user by triggering audio circuit 214 to activate the chirping sound. (In this case, the user's response to the failure would be to remove device 10 from fixture.)

If switches 218, 220 have been opened, DSP 114 enters another wait state to allow any transients in the sensor outputs to subside (step 508). As with step 502, DSP 114 determine whether switches 218, 220 remained open (step 509) before capturing (step 516) a second frame (i.e., a frame of signals obtained with sensors 102 exposed to ambient air pressure rather than being pressed against pad 310). If either switch 218, 220 is closed during this time, DSP 114 enters the failure mode (step 503). The user must then restart the calibration procedure.

The initial gain (see step 504) is applied to the signals in the second frame, and the signals are digitized and stored in memory 130, just as with the first frame. In step 510, DSP 114 processes the first frame and the second frame to find the average signal level for each frame. Before discussing this and subsequent steps in detail, it would be useful to provide some background on how preprocessing circuitry 110 generates DO signals 112.

Preprocessing circuitry 110 generates each DO signal 112 according to the following formula (equation #1):

$$DO = (V_{test}/V_{ref}) * (R_{fixed}/R_{sensor}) * 255$$

where: $V_{test}/V_{ref}$ is the Gain (i.e., amplification) applied by gain stage 118 to scale the sensor outputs to desired levels), $R_{fixed}$ is a reference resistance (which for the Tekscan array is 100,000 ohms), $R_{sensor}$ is the measured resistance of sensor 102, and 255 is the resolution of A/D converter 120. As discussed, $R_{sensor}$ is inversely proportional to the pressure (P) exerted on the sensor. With this in mind, equation #1 can be simplified as follows (equation #2):

$$DO \alpha Gain * P$$

Figure 6:
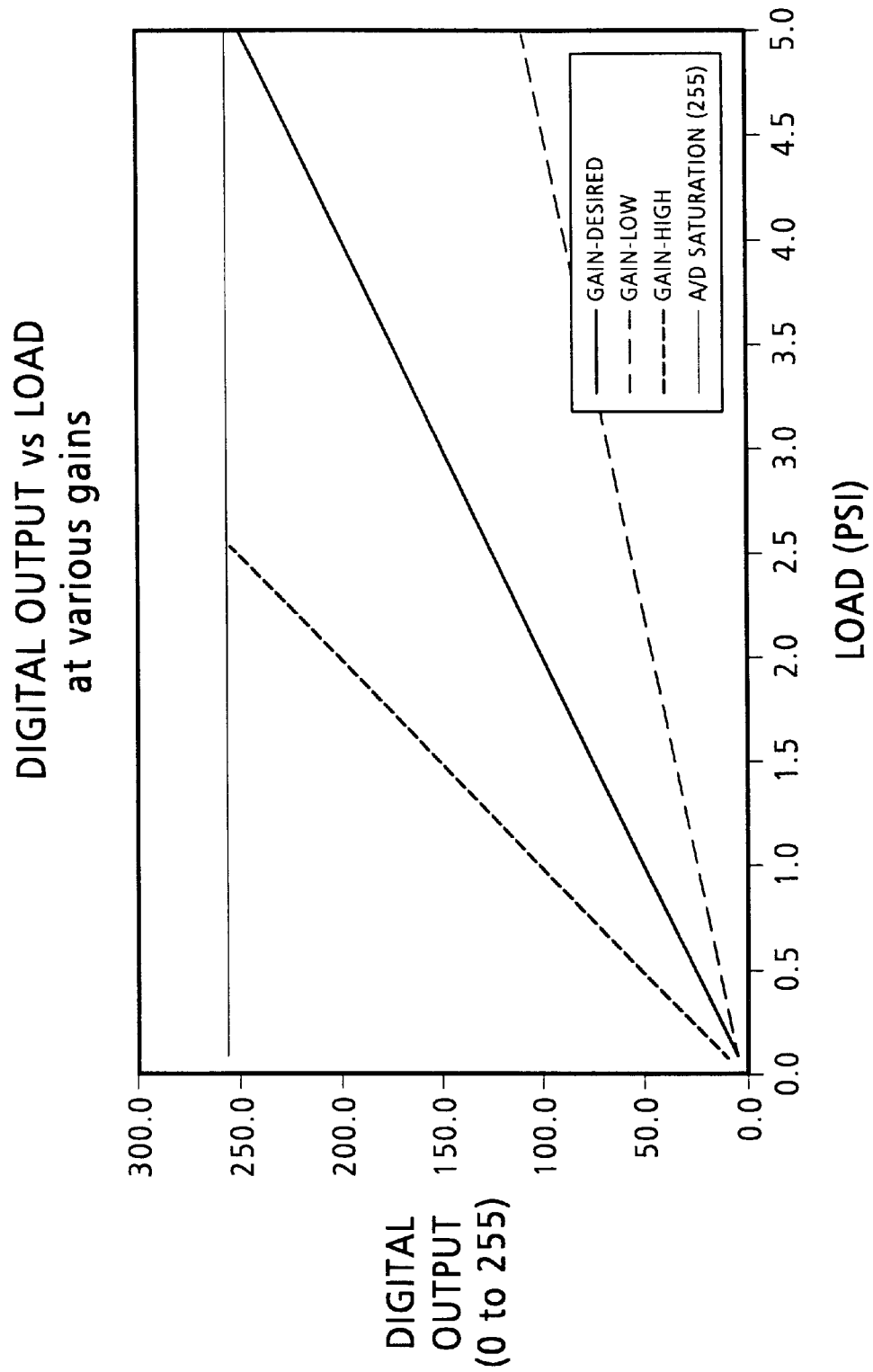
FIG. 6 shows the behavior of sensor output signals over a range of applied pressures at various gain levels.

FIG. 6 shows curves of DO vs. load (i.e., applied pressure P) at three gain levels—high, low, and desired. As can be seen each curve is linear. The maximum value of DO is set by the range of A/D converter 120 (which in this example is 8-bit binary, i.e., 0–255). Accordingly, DO values greater than 255 can not be reported. Certain adjustments of the sensor sensitivity can result in responses which would need to be reported at greater than 255. This condition is referred to as "saturation." An important goal of the calibration is to sensitize the system fully within the working range of A/D converter 120, while also avoiding saturation. Adjusting the Gain sets the effective range of A/D converter 120, thereby allowing the sensitivity of sensor array 100 to be tuned to the desired range.

As discussed above, the Gain is applied by gain stage 118 to the analog signals from sensors 102 before multiplexing, and thus the Gain affects all sensors 102 equally. In other words, the Gain adjustment performed during calibration procedure 500 is global and affects the average output of sensors 102. As can be seen from the "desired gain" curve of FIG. 5, the level of each sensor DO signal 112 should be 0 when no pressure is applied to array 100 (e.g., when tissue examination device 10 is simply exposed to ambient air pressure), and should be 50 when a pressure of 1 psi (i.e., the pressure applied using fixture 300) is applied to array 100. In other words, when properly calibrated, the digital output of each sensor 102 should be zero when the sensor is not pressed against an object, and should rise in increments of 50 for every 1 psi increment in applied pressure. This enables sensors 102 to respond accurately to applied pressures within the anticipated load range—e.g., between 0 psi (DO=0) and 5 psi (DO=250). During the calibration procedure, the Gain of gain stage 118 is adjusted based on the DO signal levels in frame one and frame two to establish these parameters on average for all sensors 102 in array 100.

Returning to FIG. 5, in step 510, DSP 114 determines the average sensor signal level of the first frame ($DO_{ave1}$) by summing the DO values for all sensors 102 in the frame and dividing the result by the number of sensors 102 in array 100. DSP 114 follows these steps to calculate the average sensor signal level of the second frame ($DO_{ave2}$). Frame averages $DO_{ave1}$ and $DO_{ave2}$ are stored in memory 130. Next, DSP 114 uses frame averages $DO_{ave1}$ and $DO_{ave2}$ to determine parameters B and M (step 511) of the following expression (equation #3):

$$DO=Gain*(MP+B)$$

where: Gain is the gain to be applied by gain stage 118 (recall that in step 504 an Initial Gain of 0.55 was set), and P is the reference pressure (i.e., 1 psi) applied to sensors 102 using fixture 300. Parameters B and M are expressed as follows (equations #4 and #5):

$$B=DO_{ave0}/\text{Initial Gain}$$

$$M=(DO_{ave1}-DO_{ave0})/(\text{Initial Gain}*P)$$

Parameters B and M are used to define a new linear gain curve (i.e., the desired gain curve of FIG. 6) for gain stage 118 that will provide sensors 102 with an average sensitivity of 50 DO/psi.

DSP 114 then determines a New Gain for gain stage 118 by inserting the expressions for B and M into equation #3 and solving the equation to provide a DO of 50 for a pressure P of 1 psi. As a result, the New Gain can be expressed as follows (equation #6):

$$\text{New Gain}=50/M$$

DSP 114 writes the New Gain to pre-processing circuitry 110 (step 512). Gain stage 118 responds by setting $V_{test}$ and $V_{ref}$ (equation #1) to implement the New Gain and provide sensors 102 with an average sensitivity of 50 DO/psi.

The second stage of the calibration—a series of equilibration actions—is performed in step 513 to improve the uniformity of the sensor response by compensating for any pre-loading of the sensors (e.g., by the stresses imposed on membrane 104 by the shape of sensor head 202). Unlike the gain adjustment for gain stage 118 described above, equilibration is applied by DSP 114 to the digital signals (DO) 112 on a sensor-by-sensor basis. Generally, equilibration is done by subtracting an offset (called "EQOFFSET") from each sensor DO signal and scaling the result by a scaling factor (called "EQSCALE"). The combined effect of these actions is to remove the preload and set the output sensitivity of every sensor 102 individually to 50 DO/psi.

The equilibration process is performed by DSP 114 as follows. First, each sensor DO signal of the first and second data frames captured in steps 505 and 516 are converted to reflect the implementation of the New Gain (set according to equation #6) by applying the following equation #7:

$$DO_{new}=DO*(\text{New Gain/Initial Gain})$$

(The new DO values for the first (1 psi) frame and the second (0 psi) frame will be referred to as $DO_{new1}$ and $DO_{new0}$, respectively.) Next, scaling factor EQSCALE and offset EQOFFSET are calculated for each sensor 102 according to the following equations #9 and #10 and stored in memory 130:

$$EQSCALE=50/(DO_{new1}-DO_{new0})$$

$$EQOFFSET=DO_{new0}$$

Then, equilibration is applied to the output DO of each sensor 102 according to the following expression (equation #11) to generate an equilibrated output ($DO_{eq}$) for each sensor:

$$DO_{eq}=EQSCALE*(DO-EQOFFSET)$$

$DO_{eq}$ values will be restrained to 0 to 255 (the range of A/D converter 120). Any values outside this range will be clipped.

DSP 114 stores in memory 130 a table T 150 (FIG. 1) that contains a matrix of the EQSCALE and EQOFFSET values calculated for each sensor 102 during equilibration step 513. During operation of tissue examination device 10 to examine tissue for underlying tissue structures (as described, e.g., in the '466 application), DSP 114 applies equation #11 individually to all sensor DO signals 112 obtained from array 100 using the EQSCALE and EQOFFSET values from the corresponding entry in table T. Put another way, the calibrated gain (New Gain) of gain stage 118 and the equilibration performed by DSP 114 cooperate result in each sensor 102 of an array 100 (having i rows and j columns) producing an equilibrated output $DO_{eq}$ defined as follows (equations #12 and #13):

$$DO_{ij}=\text{New Gain}*P_{ij}$$

and $$[DO_{eq}]_{ij}=EQSCALE_{ij}*(DO_{ij}-EQOFFSET_{ij})$$

where: $P_{ij}$ is the pressure detected by the ijth sensor 102; $DO_{ij}$ is the value of the signal after amplification according to the calibrated gain of gain stage 118; $EQSCALE_{ij}$ and $EQOFFSETT_{ij}$ are the corresponding equilibration matrix values for the ijth sensor; and $[DO_{eq}]_{ij}$ is the individually calibrated (i.e., equilibrated) value of the output signal.

Accordingly, every sensor 102 in array 100 will produce a digital output DO of 0 at no load and accurately respond to applied pressure at a sensitivity of 50/psi. Note that equations #12 and #13 are matrix relations—EQSCALE and EQOFFSET are matrices of values for each sensor 102 of the two-dimensional pressure sensor array 100. Thus, EQSCALE and EQOFFSET may be considered as error masks for the individual sensors 102 in the calibration process. This is in contrast to the "New Gain" term (calculated in 512), which is a single value that is used for all sensors 102 in array 100.

With sensors 102 calibrated as described above, the tone thresholds used to determine whether the user is applying the proper range of pressures with device 10 are adjusted to absolute DO values based on the results of the calibration. Thus, the thresholds are adjusted each time device 10 is used, thereby assuring that, e.g., wear of the sensors 102 is taken into account when determining whether the user is using device 10 properly.

Once sensors 102 are calibrated, DSP 114 performs a self check analysis 514 using the stored first and second frames. Before performing this analysis, however, DSP 114 adjusts the sensor DO signals 112 in each frame, if necessary, according to the New Gain and equilibration equations described above. The purpose of self check analysis 514 is to determine if device 10 has been damaged, if the cable connection between sensor electronics 20 and subsystem 30 has been corrupted, or if the wear of sensor array 100 has progressed to point where device 10 can no longer be effectively calibrated.

During the self check analysis, for example, DSP detects whether any rows or columns of sensors 102 in array 100 are "dead" (i.e., produce a zero output in response to the applied 1 psi pressure). DSP 114 also determines whether an excessive percentage of the sensors are either dormant (i.e., produce no or a very weak output) at the applied 0 psi and 1 psi pressures or saturated at both pressures. Limits are also established for each EQOFFSET and EQSCALE factor to determine if the corresponding sensor is saturated at the applied 0 psi and 1 psi pressures. If any of the EQOFFSET or EQSCALE factors exceed the imposed limits, the self check fails. Finally, the self check will also fail if the gain of gain stage 118 as adjusted during calibration procedure 500 exceeds a preset limit.

A self check failure puts DSP 114 into the failure mode (step 503), and DSP 114 notifies the user accordingly by activating audio circuit 214 to produce a continuous chirping sound. In the self check analysis is passed, DSP 114 enters the running (i.e., normal operating) mode 515. In this mode, DSP 114 lights green LED 212 and causes audio circuit 214 to emit a two brief chirping sounds to inform the user that device 10 is operating properly. Once the system enters the normal operating mode, the user is free to perform the tissue examination (e.g., as described in the '466 application) with device 20.

Other embodiments are within the scope of the following claims.

For example, substances other than foam pad 310 may be used. Suitable alternatives include rubber, gels, and fluid (e.g., air) filled bladders or balloons.

Figure 7:
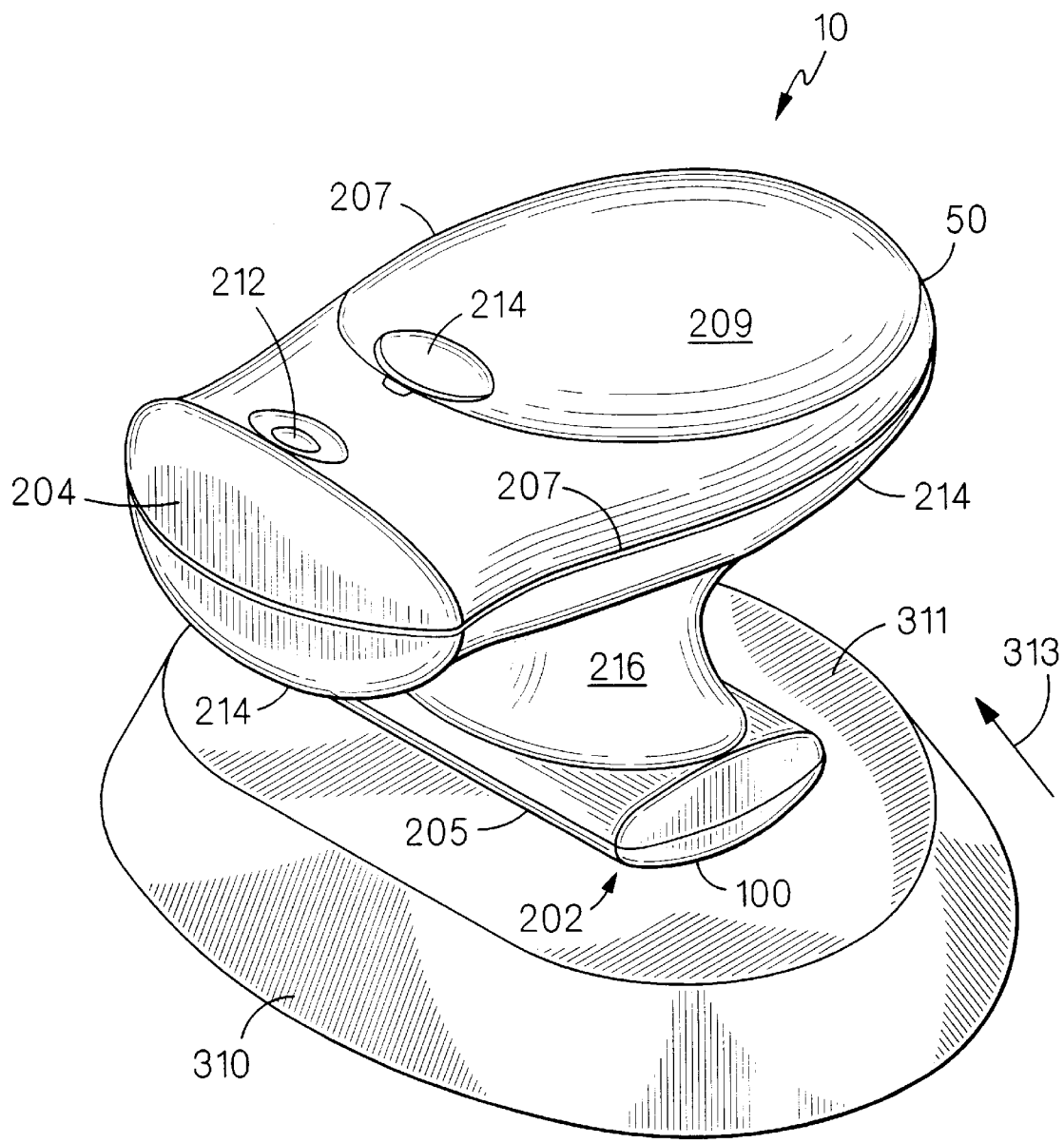
FIG. 7 shows an alternative technique for use in calibrating the tissue examination device.

Referring to FIG. 7, rather than pressing device 10 into a fixture and against the pressure-exerting substance, the user may press any of the substances described herein against the sensor head 202. For example, while holding device housing 50 stationary in one hand, the user may press pad 310 in the direction of arrow 313 against sensor head 202 to apply the selected pressure (e.g., 1 psi) uniformly to sensors 102 at pad surface 311.

Referring to FIG. 8, an alternative fixture 300' includes a recess 308' which receives sensor head 202 in a fixed position and applies a selected amount of pressure pneumatically to sensor array 100. That is, the air within recess 308 may be used as the pressure-applying substance 310'. A seal 330 is provided around the side walls of recess 308' to sealingly engage the sides of sensor head 202 and limit the amount by which sensor head 202 is inserted in recess 308'. As a result, air is trapped within recess 308'. An air supply (such as a compressor) 340 is coupled to recess 308', and is actuated by the user to pump air into recess 308' to pressurize recess to, e.g., 1 psi. A relief valve 342 is built into fixture 300 to maintain the air pressure at the desired level.

Alternatively, air supply 340 may inflate a balloon held within recess 308' against sensor head 202. In another alternative approach, a pressurized air stream may be directed at sensor array 100 to apply the selected amount of pressure uniformly to sensors 102.

In addition, although this system has been described specifically for use in a tactile examination device, the calibration procedure and devices could be employed in any pressure sensor system.

What is claimed is:

1. Apparatus for use in calibrating a tissue examination devrice of the kind that includes a plurality of pressure sensors, comprising
   a substance adapted to be engaged in a selected way by the tissue examination device and configured to apply a selected amount of pressure to the sensors when so engaged, said selected way including applying relative pressure between the tissue examination device and the substance.

2. The apparatus of claim 1 wherein said substance is adapted to have the tissue examination device pressed thereagainst to engage said substance in the selected way and cause said substance to apply the selected amount of pressure to the sensors.

3. The apparatus of claim 1 wherein said substance is adapted to be pressed against the tissue examination device to engage the device in the selected way and apply the selected amount of pressure to the sensors.

4. The apparatus of claim 1 wherein said substance is configured to apply said selected amount of pressure substantially uniformly to the plurality of sensors.

5. The apparatus of claim 1 wherein said substance includes a foam pad.

6. The apparatus of claim 1 wherein said substance includes a rubber pad.

7. The apparatus of claim 1 wherein said substance includes a gel.

8. The apparatus of claim 1 wherein said substance includes a fluid-containing balloon.

9. Apparatus for use in calibrating a tissue examination device of the kind that includes a plurality of pressure sensors, comprising
   a substance adapted to be engaged in a selected way by the tissue examination device and configured to apply a selected amount of pressure to the sensors when so engaged, said substance including pressurized air.

10. The apparatus of claim 1 further comprising a fixture that supports said substance.

11. Apparatus for use in calibrating a tissue examination device of the kind that includes a plurality of pressure sensors, comprising
   a substance adapted to be engaged in a selected way by the tissue examination device and configured to apply a selected amount of pressure to the sensors when so engaged, and
   a fixture that supports said substance, said fixture including a recess configured to receive a head of the tissue examination device on which the sensors are mounted, said substance being disposed in said recess.

12. The apparatus of claim 11 wherein said fixture is configured to allow the head of the tissue examination device to be advanced by a selected distance into said recess.

13. The apparatus of claim 12 wherein said substance is configured to be deflected by the head of the tissue examination device when it is advanced by the selected distance, thereby to apply said selected amount of pressure to the sensors.

14. The apparatus of claim 11 wherein said substance includes air and further comprising
   a seal disposed around a portion of the recess for engagement by the head of the tissue examination device, and
   an air supply configured to pressurize the air in said recess to apply said selected amount of pressure to the sensors.

15. The apparatus of claim 12 wherein said fixture includes a portion configured to engage another portion of the tissue examination device when the head of the tissue examination device has been advanced by the selected distance to limit further advancement of the head.

16. The apparatus of claim 15 wherein said portion of said fixture comprises a projection disposed on a surface of said fixture in which said recess is disposed.

17. The apparatus of claim 16 wherein the tissue examination device includes a handle attached to the head, said surface of said fixture being configured to receive a portion of the handle when the head is received in said recess.

18. The apparatus of claim 11 wherein the tissue examination device includes a power switch, a portion of said fixture being configured to actuate the power switch when the head is received in said recess.

19. The apparatus of claim 1 wherein the sensors of the tissue examination device are of a kind that produce signals in response to pressure imposed thereon as the sensors are pressed against tissue, and further comprising circuitry for calibrating the sensors based on levels of the signals produced by the sensors in response to said selected amount of pressure imposed by said substance.

20. The apparatus of claim 19 wherein said circuitry is configured to perform the calibration for the plurality of sensors as a whole based on the levels of the signals produced by the sensors in response to said selected amount of pressure.

21. Apparatus for use in calibrating a tissue examination device of the kind that includes a plurality of pressure sensors that produce signals in response to pressure imposed thereon as the sensors are pressed against tissue, comprising a substance adapted to be enraged in a selected way by the tissue examination device and configured to apply a selected amount of pressure to the sensors when so engaged, and circuitry for calibrating the sensors based on levels of the signals produced by the sensors in response to said selected amount of pressure imposed by said substance, said circuitry being configured to perform the calibration for the plurality of sensors as a whole based on the levels of the signals produced by the sensors in response to said selected amount of pressure, said circuitry being further configured to perform the calibration to cause calibrated signals to be generated based on the signals produced by the sensors, said calibrated signals having levels that change by a selected average amount in response to a selected amount of change in the pressure imposed on the sensors.

22. Apparatus for use in calibrating a tissue examination device of the kind that includes a plurality of pressure sensors that produce signals in response to pressure imposed thereon as the sensors are pressed against tissue, comprising a substance adapted to be engaged in a selected way by the tissue examination device and configured to apply a selected amount of pressure to the sensors when so engaged, and circuitry for calibrating the sensors based on levels of the signals produced by the sensors in response to said selected amount of pressure imposed by said substance, said circuitry being configured to perform the calibration for the plurality of sensors individually based on the levels of the signals produced by the sensors in response to said selected amount of pressure.

23. The apparatus of claim 22 wherein said circuitry is configured to perform the calibration to cause calibrated signals to be generated based on the signals produced by the sensors, each one of said calibrated signals having a selected range of levels that corresponds to a selected range of applied pressures.

24. The apparatus of claim 23 wherein the selected range of levels for each of the sensors is between a zero level that corresponds to the applied pressure when the sensor is not pressed against tissue, and a maximum level that corresponds to a maximum expected applied pressure when the sensor is pressed against tissue that contains an underlying tissue structure to be detected by the tissue examination device.

25. Apparatus comprising a tissue examination device that includes a plurality of pressure sensors that produce signals in response to pressure imposed thereon as the sensors are pressed against tissue, and a processor for processing said signals to detect whether an underlying tissue structure is present in the tissue being examined, and a calibration device adapted to be engaged with said tissue examination device in a selected way to enable said calibration device to perform a calibration operation on said sensors, said calibration device being configured to cause operating power to be applied to said processor only when engaged with said tissue examination device in said selected way.

26. The apparatus of claim 25 wherein said tissue examination device includes a power switch for the processor, a portion of said calibration device being configured to actuate the power switch when said tissue examination device is engaged with said calibration device in said selected way.

27. The apparatus of claim 25 wherein said calibration device includes a fixture having a recess configured to receive a head of the tissue examination device on which the sensors are mounted, and a substance disposed in said recess configured to apply a selected amount of pressure to said sensors when said head is disposed in said recess.

28. The apparatus of claim 27 wherein said tissue examination device includes a power switch for the processor, a portion of said fixture being configured to actuate the power switch when said head of said tissue examination device is disposed in said recess in the selected way.

29. Apparatus comprising a tissue examination device including a plurality of pressure sensors mounted on a sensor head, each of said sensors producing signals in response to pressure imposed thereon as the sensor is pressed against tissue, and a processor for processing said signals to detect whether an underlying tissue structure is present in the tissue being examined, and a calibration device for said tissue examination device, said calibration device including a substance adapted to be engaged in a selected way by the sensor head and configured to apply a selected amount of pressure to the sensors when so engaged, and circuitry for calibrating said sensors based on the levels of the signals that are produced by said sensors in response to said selected amount of pressure imposed by said substance.

30. The apparatus of claim 29 wherein said circuitry is configured to perform the calibration for the plurality of sensors as a whole based on the levels of the signals produced by the sensors in response to said selected amount of pressure.

31. The apparatus of claim 30 wherein said circuitry is configured to perform the calibration to cause calibrated signals to be generated based on the signals produced by said sensors, said calibrated signals having levels that change by a selected average amount in response to a selected amount of change in the pressure imposed on the sensors.

32. The apparatus of claim 30 wherein said circuitry is further configured to perform the calibration for the plurality of sensors individually based on the levels of the signals produced by the sensors in response to said selected amount of pressure.

33. The apparatus of claim 32 wherein said circuitry is configured to perform the calibration to cause calibrated signals to be generated based on the signals produced by the sensors, each one of said calibrated signals having a selected range of levels that corresponds to a selected range of applied pressures.

34. The apparatus of claim 33 wherein the selected range of levels for each of the sensors is between a zero level that corresponds to the applied pressure when the sensor is not pressed against tissue, and a maximum level that corresponds to a maximum expected applied pressure when the sensor is pressed against tissue that contains an underlying tissue structure to be detected by the tissue examination device.

35. The apparatus of claim 29 further comprising
circuitry for acquiring a first set of said signals from said sensors when said head is engaged with said substance and said selected amount of pressure has been imposed on said sensors thereby, and acquiring a second set of said signals from said sensors when said when said head is not engaged with said substance, said calibrating circuitry being further configured to calibrate said sensors based on said first set of signals and said second set of signals, and
a memory for storing said first set of signals and said second set of signals.

36. The apparatus of claim 35 wherein said acquiring circuitry is configured to apply a gain to the signal acquired by each one of said sensors, said calibrating circuitry being further configured to perform a first calibration operation that includes:
determining a calibrated gain based on said first set of signals and said second set of signals, and
changing said gain to said calibrated gain thereby to calibrate said plurality of sensors as a whole.

37. The apparatus of claim 36 wherein said calibrating circuitry is further configured to determine an average level of said first set of signals and an average level of said second set of signals, and to determine said calibrated gain based on average levels.

38. The apparatus of claim 36 wherein said calibrating circuitry is further configured to determine individual correction factors for individual ones of said sensors based on said first set of signals and said second set of signals, and to store said correction factors in said memory.

39. The apparatus of claim 38 wherein said processor is further configured to apply said correction factors to said signals generated by said sensors when said tissue examination device is pressed against tissue to generate corrected signals, and to process said corrected signals to detect whether an underlying tissue structure is present in the tissue being examined.

40. The apparatus of claim 39 further comprising circuitry responsive to said processor for notifying a user of the tissue examination device if an underlying tissue structure has been detected.

41. The apparatus of claim 29 wherein said calibration circuitry is further configured to determine if the calibration was successful and, if so, notifying a user of the tissue examination device that examination of tissue may proceed.

42. The apparatus of claim 41 wherein said calibrating circuitry is further configured to disable said processor from further operation if said circuitry determines that the calibration has been unsuccessful.

43. A method for calibrating a tissue examination device of the kind that includes a plurality of pressure sensors, comprising
providing a substance adapted to be engaged in a selected way by the tissue examination device, and
engaging the substance with the tissue examination device in the selected way to cause the substance to apply a selected amount of pressure to the sensors.

44. The method of claim 43 wherein said engaging step includes pressing the tissue examination device against the substance to cause the substance to apply the selected amount of pressure to the sensors.

45. The method of claim 43 wherein said engaging step includes pressing the substance against the tissue examination device to cause the substance to apply the selected amount of pressure to the sensors.

46. The method of claim 43 further comprising causing said substance to apply the selected amount of pressure substantially uniformly to the plurality of sensors.

47. The method of claim 43 further comprising
providing a fixture having a recess configured to receive a head of the tissue examination device on which the sensors are mounted, said substance being disposed in said recess,
said engaging step including inserting the head of the tissue examination device into the recess.

48. The method of claim 47 further comprising advancing the head of the tissue examination device by a selected distance into said recess to deflect the substance and cause the substance to apply said selected amount of pressure to the sensors.

49. The method of claim 47 wherein said substance includes air and further comprising
sealingly engaging the head of the tissue examination device within the recess, and
pressurizing the air in the recess to apply said selected amount of pressure to the sensors.

50. The method of claim 48 further comprising engaging a portion of the fixture with another portion of the tissue examination device when the head of the tissue examination device has been advanced by the selected distance to limit further advancement of the head.

51. The method of claim 47 wherein the tissue examination device includes a power switch, and further comprising actuating the power switch with a portion of the fixture when the head is inserted in the recess.

52. The method of claim 43 wherein the sensors of the tissue examination device are of a kind that produce signals in response to pressure imposed thereon as the sensors are pressed against tissue, and further comprising
calibrating the sensors based on levels of the signals produced by the sensors in response to said selected amount of pressure imposed by said substance.

53. The method of claim 52 further comprising performing said calibrating for the plurality of sensors as a whole based on the levels of the signals produced by the sensors in response to said selected amount of pressure.

54. The method of claim 53 further comprising performing said calibrating to cause calibrated signals to be generated based on the signals produced by the sensors, said calibrated signals having levels that change by a selected average amount in response to a selected amount of change in the pressure imposed on the sensors.

55. The method of claim 52 further comprising performing said calibrating for the plurality of sensors individually based on the levels of the signals produced by the sensors in response to said selected amount of pressure.

56. The method of claim 55 further comprising performing said calibrating to cause calibrated signals to be generated based on the signals produced by the sensors, each one of said calibrated signals having a selected range of levels that corresponds to a selected range of applied pressures.

57. The method of claim 56 wherein the selected range of levels for each of the sensors is between a zero level that corresponds to the applied pressure when the sensor is not pressed against tissue, and a maximum level that corresponds to a maximum expected applied pressure when the sensor is pressed against tissue that contains an underlying tissue structure to be detected by the tissue examination device.

58. A method of calibrating a tissue examination device that includes a plurality of pressure sensors that produce signals in response to pressure imposed thereon as the sensors are pressed against tissue, and a processor for processing said signals to detect whether an underlying tissue structure is present in the tissue being examined, said method comprising the steps of engaging the tissue examination device with a calibration device in a selected way enable the calibration device to perform a calibration operation on said sensors, and applying operating power to said processor only when the calibration device is engaged with the tissue examination device in said selected way.

59. The method of claim 58 wherein said tissue examination device includes a power switch for the processor, and further comprising actuating the power switch when the tissue examination device is engaged with said calibration device in the selected way.

60. A method comprising providing a tissue examination device including a plurality of pressure sensors mounted on a sensor head, each of said sensors producing signals in response to pressure imposed thereon as the sensor is pressed against tissue, and a processor for processing said signals to detect whether an underlying tissue structure is present in the tissue being examined, providing a calibration device that includes a substance adapted to be engaged by the sensor head, engaging the sensor head with the substance in a selected way to cause the substance to apply a selected amount of pressure to the sensors, and calibrating the sensors based on the levels of the signals that are produced by said sensors in response to the selected amount of pressure imposed by the substance.

61. The method of claim 60 further comprising performing said calibrating for the plurality of sensors as a whole based on the levels of the signals produced by the sensors in response to said selected amount of pressure.

62. The method of claim 61 further comprising performing said calibrating to cause calibrated signals to be generated based on the signals produced by said sensors, said calibrated signals having levels that change by a selected average amount in response to a selected amount of change in the pressure imposed on the sensors.

63. The method of claim 60 further comprising performing said calibrating for the plurality of sensors individually based on the levels of the signals produced by the sensors in response to said selected amount of pressure.

64. The method of claim 63 further comprising performing said calibrating to cause calibrated signals to be generated based on the signals produced by the sensors, each one of said calibrated signals having a selected range of levels that corresponds to a selected range of applied pressures.

65. The method of claim 64 wherein the selected range of levels for each of the sensors is between a zero level that corresponds to the applied pressure when the sensor is not pressed against tissue, and a maximum level that corresponds to a maximum expected applied pressure when the sensor is pressed against tissue that contains an underlying tissue structure to be detected by the tissue examination device.

66. The method of claim 60 further comprising acquiring a first set of said signals from said sensors when said head is engaged with said substance and said selected amount of pressure has been imposed on said sensors thereby, and acquiring a second set of said signals from said sensors when said when said head is not engaged with said substance, performing said calibrating based on said first set of signals and said second set of signals, and storing said first set of signals and said second set of signals in a memory.

67. The method of claim 66 further comprising applying a gain to the signal acquired by each one of said sensors, said calibrating step including a first calibration operation that includes:

determining a calibrated gain based on said first set of signals and said second set of signals, and changing said gain to said calibrated gain thereby to calibrate said plurality of sensors as a whole.

68. The method of claim 67 said calibrating step further includes determining an average level of said first set of signals and an average level of said second set of signals, and determining said calibrated gain based on average levels.

69. The method of claim 67 wherein said calibrating step further includes determining individual correction factors for individual ones of said sensors based on said first set of signals and said second set of signals, and storing said correction factors in said memory.

70. The method of claim 69 further comprising causing said processor to apply said correction factors to said signals generated by said sensors when said tissue examination device is pressed against tissue to generate corrected signals, and to process said corrected signals to detect whether an underlying tissue structure is present in the tissue being examined.

71. The method of claim 70 further comprising notifying a user of the tissue examination device if an underlying tissue structure has been detected.

72. The method of claim 60 further comprising determining if the calibration was successful and, if so, notifying a user of the tissue examination device that examination of tissue may proceed.

73. The method of claim 72 further comprising disabling the processor from further operation if the calibration is determined to have been unsuccessful.

* * * * *